United States Patent [19]
Donzier et al.

[11] Patent Number: 5,509,312
[45] Date of Patent: Apr. 23, 1996

[54] DIAPHRAGM PRESSURE SENSOR INCLUDING ANTI-STOCK PROTECTION MEANS AND GRADIOMANOMETER INCORPORATING SUCH A SENSOR

[75] Inventors: Eric P. Donzier, Blandy les Tours; Fadhel Rezgui, Sceaux, both of France

[73] Assignee: Schlumberger Technology Corporation, Houston, Tex.

[21] Appl. No.: 249,122

[22] Filed: May 25, 1994

[30] Foreign Application Priority Data

May 25, 1993 [FR] France .................... 93 06185

[51] Int. Cl.$^6$ ................................. G01L 9/06
[52] U.S. Cl. ................................. 73/706; 73/155
[58] Field of Search ................ 73/706, 707, 715, 73/721, 727, 155–155

[56] References Cited

U.S. PATENT DOCUMENTS

| | | | |
|---|---|---|---|
| 3,616,688 | 11/1971 | Roussin et al. | 73/151 |
| 4,135,408 | 1/1979 | Di Giovanni | 73/721 |
| 4,195,349 | 3/1980 | Balkanli | 73/152 |
| 4,452,069 | 6/1984 | Hattori et al. | 73/707 |
| 4,507,971 | 4/1985 | Vachek | 73/707 |
| 4,553,428 | 11/1985 | Upchurch | 73/152 |
| 4,637,000 | 1/1987 | Thigpen et al. | 73/707 |
| 4,805,449 | 2/1989 | Das | 73/151 |
| 5,024,098 | 6/1991 | Petitjean et al. | 73/151 |
| 5,092,177 | 3/1992 | Varacca | 73/721 |
| 5,163,321 | 11/1992 | Perales | 73/151 |
| 5,170,018 | 12/1992 | Potier | 73/151 |
| 5,184,508 | 2/1993 | Desbrandes | 73/152 |
| 5,209,120 | 5/1993 | Araki | 73/706 |
| 5,257,546 | 11/1993 | Tobita et al. | 73/721 |
| 5,337,822 | 8/1994 | Massie et al. | 73/155 |

FOREIGN PATENT DOCUMENTS 0621981  8/1978  U.S.S.R. .................... 73/707

*Primary Examiner*—Richard Chilcot
*Assistant Examiner*—Jewel V. Artis
*Attorney, Agent, or Firm*—John H. Bouchard

[57] ABSTRACT

A pressure sensor (20) comprises a deformable diaphragm (22) which closes a fluid passage (18) in sealed manner. In order to protect the diaphragm (22) from shocks, the passage includes a restriction (44) whose dimensions are so designed as to limit the pressure peak applied to the diaphragm to a cutoff value which the diaphragm can withstand. The restriction (44) may be formed in a detachable capillary tube (42) or it may be in the form of grooves in a small silicon plate integrated in the active portion of the sensor.

20 Claims, 3 Drawing Sheets

DIAPHRAGM PRESSURE SENSOR INCLUDING ANTI-STOCK PROTECTION MEANS AND GRADIOMANOMETER INCORPORATING SUCH A SENSOR

BACKGROUND OF THE INVENTION

1. Field of the Invention

This invention concerns a deformable diaphragm pressure sensor with integrated anti-shock protection means. The invention also relates to a gradiomanometer incorporating such a sensor.

2. The Related Art

The pressure sensor in accordance with the invention may be used in any situation in which the use of a sensor, and especially its handling, involves a high risk of shocks which can lead to the deformable diaphragm bursting. Applications involving this risk occur particularly in the oil industry, in which the handling effected at the wellhead in particular often results in the rods and tools which are inserted into the well being dropped. Thus a differential pressure sensor in accordance with the invention can be used in gradiomanometers serving to measure the density of the fluid present in oil boreholes or wells, and also in apparatus for measuring the speed of displacement of a fluid.

In order to effect pressure measurements in oil wells it is known to use pressure sensors in which the sensitive element is formed by a diaphragm adapted to deform when a very small pressure difference exists between the two sides of the diaphragm. The measurement of the deformation of the diaphragm is effected by means of a bridge of piezo-resistive strain gages associated with the diaphragm.

In French patent application No. 93 04228, a very sensitive pressure sensor is proposed, using a very thin silicon diaphragm (for example around 30 µm), on which the bridge of strain gages is formed using technologies comparable with those used in microelectronics.

In such a pressure sensor, the deformable diaphragm closes in sealed manner a passage containing a liquid such as a silicone oil of known density which transmits in full the pressures obtaining at the two ends of the passage. The diaphragm is thus biased or loaded with a fluid column of a certain height, which represents an applied pressure on the diaphragm.

When the tool in which the pressure sensor is fitted suffers a shock, for example because the tool has fallen a few centimeters, the fluid column is accelerated, which results in the application of a peak pressure to the diaphragm for the duration of the shock (in the order of a few µs to a few ms), with an amplitude depending on the height of the fall and on the duration of the shock. Thus a fall of 10 cm on to a solid floor (concrete for example) results in a pressure peak of 10 bars for some tens of milliseconds on a diaphragm loaded with a column of 0.5 m.

Having regard to the measurement range of the diaphragm (some tenths of a bar), it will be understood that in such situations the diaphragm is destroyed. In view of the handling conditions at wellheads, this fragility of existing pressure sensors to shock results in a considerable increase in the cost of measurements effected with the aid of such sensors, which cannot in general be used without being often irreversibly damaged.

U.S. Pat. No. 3 616 688 describes a gradiomanometer for an oil well. In order to detect the pressure difference between two points separated by a known vertical distance, equipment is used that is vertically movable inside a tubular body disposed in a well. That movable equipment is filled with liquid and comprises two deformable bellows connected together by a rigid tube. The vertical position of the movable equipment inside the tubular body is a function of the static pressure difference exerted by the fluid present in the well on the two bellows. The pressure differential is thus determined by measuring the position of the movable equipment in the tubular body. An expansion chamber bounded by a third bellows communicates through a restriction with the lower bellows, in order to absorb variation in the volume of liquid contained in the movable equipment, without affecting the dynamic operation of the movable equipment.

The device described in U.S. Pat. No. 3 616 688 is also sensitive to shocks. Thus, the considerable pressure which is applied to the lower bellows of the movable equipment risks permanent deformation of the bellows and error in the measurements subsequently effected. In that document it is proposed to overcome the problem by fitting a normally-closed valve in parallel with the restriction which connects the lower bellows of the movable equipment to the bellows of the expansion chamber, which valve opens automatically when a downwards acceleration peak is applied to the apparatus as a result of a shock.

Given the totally different natures of the pressure sensors, the solution proposed in U.S. Pat. No. 3 616 688 is clearly not applicable to a deformable diaphragm pressure sensor.

SUMMARY OF THE INVENTION

A particular object of this invention is to provide a deformable diaphragm pressure sensor whose novel design enables it to withstand relatively large shocks without the shocks resulting in the diaphragm bursting or in any damage whatsoever to the sensor.

According to the invention, this result is achieved by means of a pressure sensor comprising a deformable diaphragm closing a fluid passage in sealed manner, and means for measuring deformation of the diaphragm, said passage including a restriction so designed as to co-operate with the diaphragm to form a lowpass filter with a determined cutoff frequency.

The presence of a restriction in the passage containing the fluid which applies the pressure to the deformable diaphragm results in the pressure wave in the region of the diaphragm being attenuated. The residual pressure transmitted to the deformable diaphragm is limited to a value low enough to ensure that the integrity of the diaphragm is preserved. This attenuation depends on the geometrical dimensions of the restriction and of the diaphragm and also on the viscosity of the fluid.

More specifically, if the dimensions of the restriction are related to those of a circular orifice of radius $r_c$ (in mm) and of length $l$ (in mm), they advantageously satisfy the equation:

$$(r_c^4)/l = (2 \cdot n \cdot r_s^6 \cdot f_o)/(E \cdot e^3)$$

where:
n is the viscosity of the fluid at ambient temperature (in Pa.s);
$r_s$ is the useful radius of the diaphragm (in mm);
$f_o$ is the cutoff frequency (in Hz) adopted for the sensor;
E is the Young's modulus (in Pa) of the diaphragm; and
e is the thickness of the diaphragm (in mm).

In order to ensure operation of the sensor under normal conditions of movement thereof inside a well, while avoiding the diaphragm bursting in the event of shock, the cutoff frequency $f_o$ lies between a maximum frequency for normal operation of the sensor and a maximum mechanically-acceptable frequency for the diaphragm. Thus the cutoff frequency may be equal to not more than 100 Hz and, for example, may be in the region of 10 Hz at ambient temperature.

In a preferred embodiment of the invention, the deformable diaphragm is mounted in a rigid tubular support delimiting a section of said passage internally, the restriction being formed in this section.

The restriction may in particular be formed by a detachable capillary tube mounted in the said section of the passage. This design makes it possible either to unblock the capillary tube or to replace it. However, the manufacturing conditions of the capillary tube put a minimum value on section of the restriction.

When the rigid tubular support has a radial surface on which the deformable diaphragm is fixed, either directly or via a decoupling part with a central opening which communicates with the aforesaid section of the passage, the restriction may be in the form of one or more grooves. The groove or grooves can be formed in a small plate fixed either to the radial surface of the support or to the central portion of the decoupling part, when present. The groove or grooves can equally well be formed directly in the radial surface of the support or in the central portion of the decoupling part. They place the passage through the tubular support in communication with a peripheral edge of the small plate. In this case, the restriction is not detachable but it is possible to make restrictions with very precise dimensions with a section that is hardly subject to any lower limit. Thus the deformable diaphragm, the decoupling part, if present, and the small plate may be implemented in silicon, the groove or grooves forming the restriction being obtained using technologies comparable to those which are used in micro-electronics.

Taking into account the features of the two above-described implementations, a detachable capillary tube is preferably used when the diameter of the restriction is sufficiently large to allow its manufacture by conventional techniques. Otherwise, the restriction should be formed by one or more grooves formed in a small plate, in accordance with the second implementation proposed above.

BRIEF DESCRIPTION OF THE DRAWINGS

Two embodiments of the invention will now be described as non-limiting examples, with reference to the accompanying drawings, in which.

DESCRIPTION OF THE PREFERRED EMBODIMENTS

Figure 1:
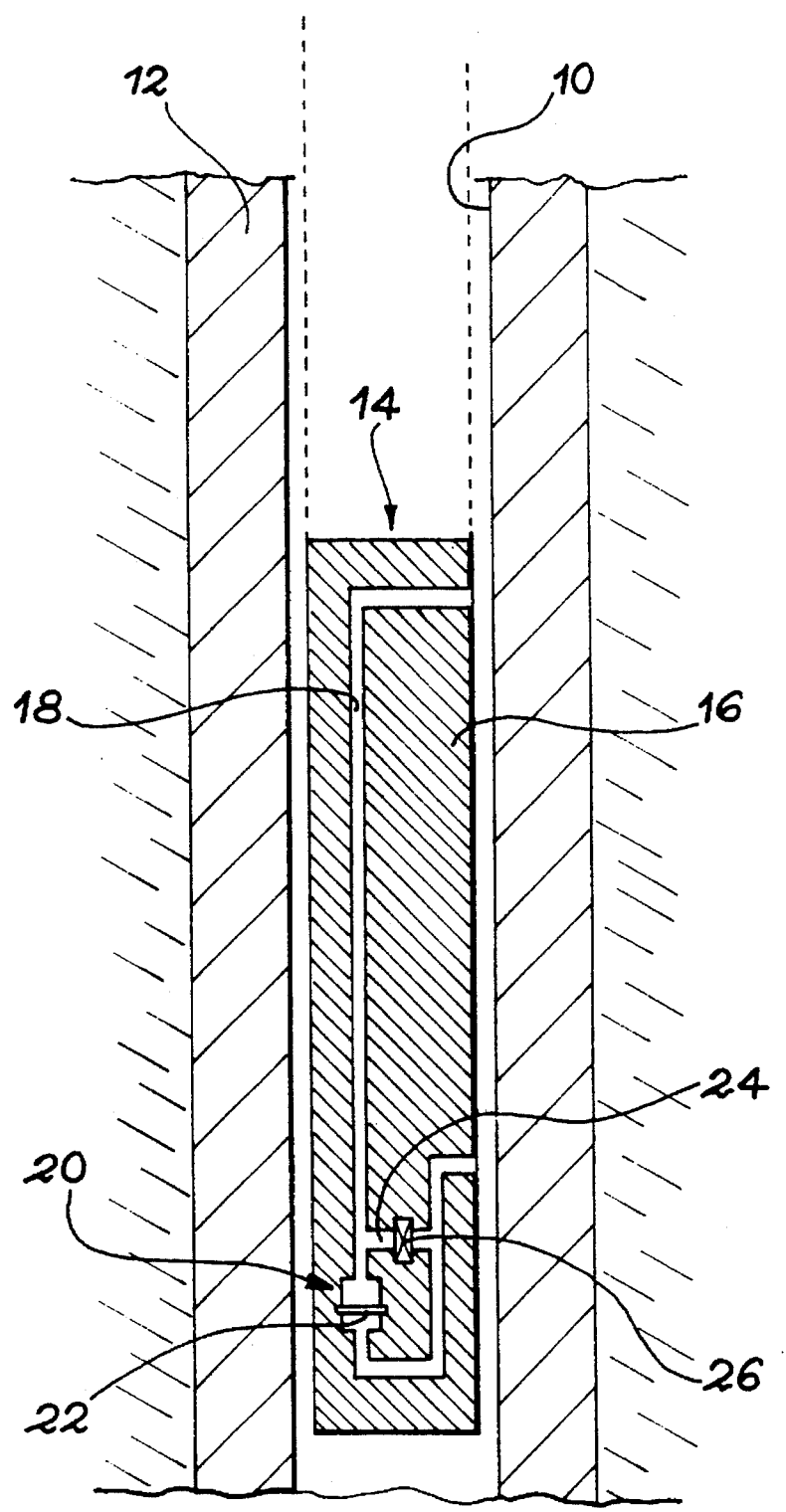
FIG. 1 is a schematic longitudinal section through a gradiomanometer disposed in an oil well, in order to effect density measurements.

FIG. 1 shows a section of an oil well 10, bounded by casing 12. In order that the exploitation of the well may be effected under the best conditions, it is necessary within the well to distinguish regions containing water, regions which contain oil in the liquid state, and regions which contain oil in the gaseous state.

In order to effect this distinction, a gradiomanometer 14 is lowered into the well 10, whereby the density of the fluid present in the well can be measured over the whole height of the well traversed by this apparatus. The gradiomanometer 14 is suspended on a cable (not shown in FIG. 1), which allows it to be lowered and then raised again, and which also allows transmission to the surface of signals representing the density of the fluid, which signals are generated by the apparatus.

The gradiomanometer 14 comprises a cylindrical body 16, in which a passage 18 is formed that is filled with a reference liquid of known density, such as a silicone oil. The ends of the passage 18 open at two different levels in the body 16. The difference between these levels corresponds to a known height, h, for example around 0.5 m.

A differential pressure sensor 20 is located in the passage 18. This sensor comprises a deformable diaphragm 22 which closes the passage 18 in sealed manner and keeps the liquid in place therein, in conjunction with the pressure which reigns in the well around the gradiomanometer 14. The value of this pressure varies with the depth at which the apparatus is located but may reach around 1000 bars.

If the density of the reference liquid present in the passage 18 is denoted $\rho_O$ and the density of the fluid present in the well at the level where the gradiomanometer 14 is located is denoted $\rho_x$, the diaphragm 22 of the differential pressure sensor 20 is subjected to a pressure difference $\Delta\rho$ given by the formula:

$$\Delta\rho = (\rho_O - \rho_x) \cdot g \cdot h \cdot \cos\Theta$$

where:

g represents the magnitude of the local gravity field; and $\Theta$ is the angle of inclination of the well relative to vertical.

This formula shows clearly that the difference in pressure experienced by the diaphragm 22 of the sensor 20 is representative of the density $\rho_x$ of the fluid present in the well.

The gradiomanometer preferably further comprises a bypass duct 24 inside the body 16, connected to the passage 18 upstream and downstream of the pressure sensor 20. A normally closed valve 26 is located in the bypass duct 24. The valve 26 is designed to open under the effect of a shock, in order to avoid damage to the diaphragm. However, its response time is relatively long, so that it fulfills this role only very imperfectly and, in practice, it does not prevent the diaphragm 22 bursting in the case of shock in differential pressure sensors of conventional design.

In order to overcome this problem and to ensure efficient protection of the diaphragm 22 of the sensor, it is proposed in accordance with the invention to equip this sensor with integrated anti-shock protection means which can take various forms, two examples of which are described in turn below with reference firstly to FIG. 2 and then to FIGS. 3 and 4.

Figure 2:
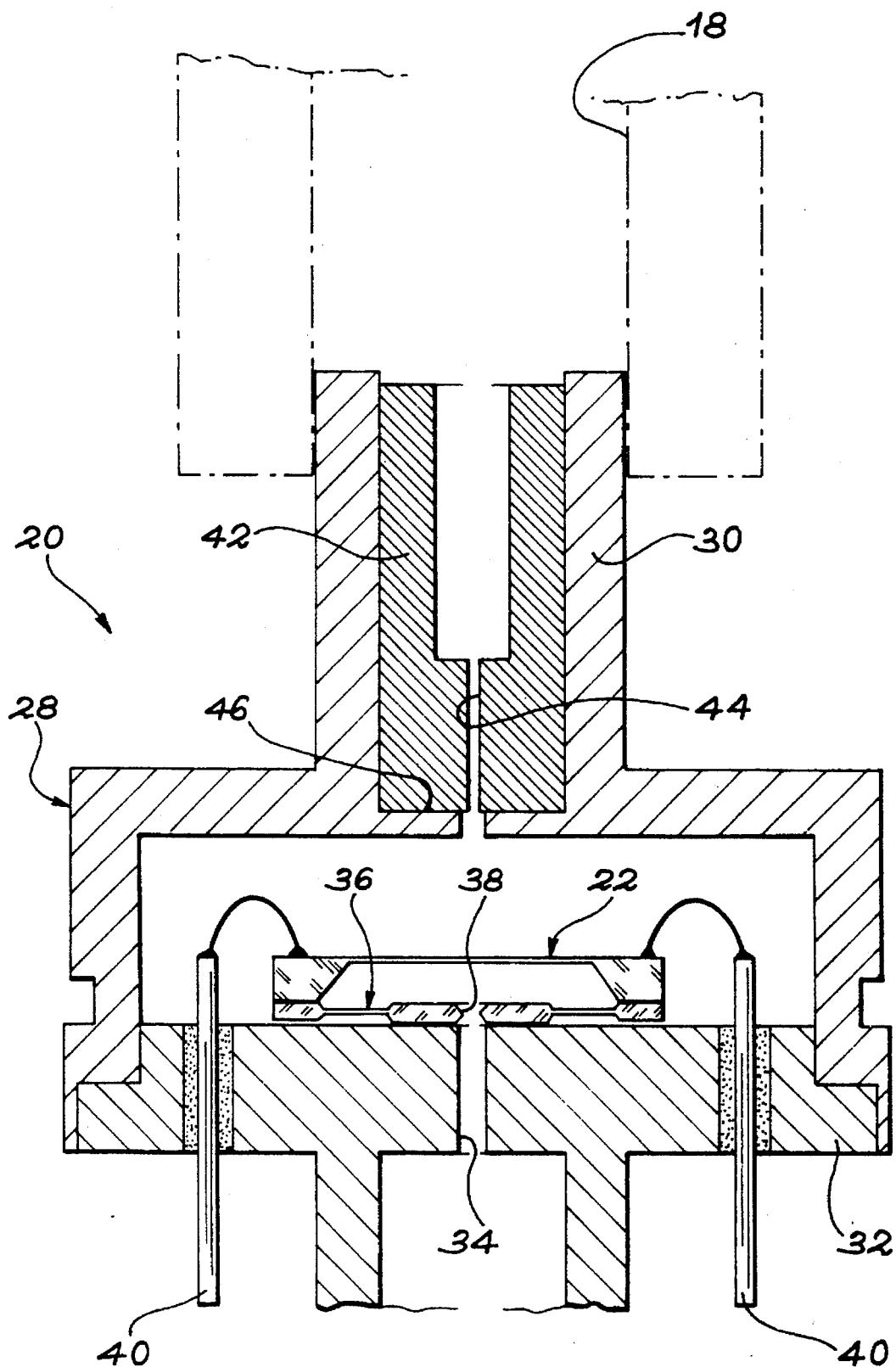
FIG. 2 is a vertical section of a differential pressure sensor used in the gradiomanometer of FIG. 1 and constituting a first embodiment of the invention.

In the embodiment shown in FIG. 2, the differential pressure sensor 20 comprises a rigid tubular support 28 formed by the sealed assembly of a tubular part 30 and a part 32 in the form of a disk. More particularly, the tubular part 30 has a section of relatively small diameter and a section of relatively large diameter and the part 32 in the form of a disk is connected in sealed manner to the relatively large diameter section of the tubular part 30. In particular, the parts 30 and 32 forming the rigid tubular support 28 may be made from a material such as "Kovar" (Trade Mark).

The rigid tubular support 28 is mounted in sealed manner in the passage 18 so as to bound a section of this passage internally. To this end the part 32 in the form of a disk is traversed at its center by a circular hole 34. The fitting of the rigid tubular support 28 is advantageously effected in detachable manner, in order to allow replacement of the differential pressure sensor 20, when this proves necessary.

The part 32 in the form of a disk comprises a flat surface facing the tubular part 30 and orientated perpendicularly to the axis of the passage 18. The deformable diaphragm 22 of the sensor 20 is fixed in sealed manner on this flat surface of the part 32 in the form of a disk. More specifically, the flat surface of the part 32 in the form of a disk supports the deformable diaphragm 22 via a decoupling part 36.

The decoupling part 36 is a thin, flat plate, for example of square shape, advantageously formed of silicon by techniques like those commonly used in microelectronics (oxidation, photo-lithography, anisotropic micro-machining, etc.). This decoupling part 36 has a central opening 38 located in the extension of the hole 34. Its central portion adjacent the opening 38 is bonded to the upper surface of the part 32 in the form of a disk.

The deformable diaphragm 22 is likewise advantageously formed from a small silicon plate using the techniques of micro-machining commonly employed in the field of microelectronics. It has the shape of a flat, square plate whose outer dimensions are identical to those of the decoupling part 36.

The deformable diaphragm 22 is fixed in sealed manner on the decoupling part 36 by bonding the peripheral region of the diaphragm on to the adjacent peripheral zone of the decoupling part.

In order to detect and measure the deformations of the deformable diaphragm 22, measuring means are used which comprise a bridge of piezo-resistive strain gages (not shown) formed for example on the upper face of the diaphragm 22. This bridge of piezo-resistive strain gages can be made during the fabrication of the deformable diaphragm, utilizing conventional micro-electronics techniques. It comprises four resistors located in pairs in two orthogonal directions, together with electrically conducting connections connecting the resistors to form the bridge of strain gages. Contacts formed on the upper face of the diaphragm allow the bridge of strain gages to be connected to an electronics box (not shown) by electrical conductors 40 soldered to the contacts and passing through the part 32 in the form of a disk in sealed manner.

In the embodiment shown in FIG. 2, the differential pressure sensor 20 comprises integrated anti-shock protection means in the form of a capillary tube 42 mounted in the relatively small diameter section of the tubular part 30. This capillary tube 42 is in the form of a stainless steel tube traversed along its axis by a restriction 44. It is detachably mounted in the relatively small diameter section of the tubular part 30, for example by means of a cap (not shown) that is screwed to the end of the part 30 opposite the part 32 in the form of a disk. This cap holds the capillary tube 42 in abutment against a shoulder 46 formed inside the part 30.

The detachable nature of the capillary tube 42 allows it to be cleaned or replaced as necessary.

The dimensions of the restriction 44, i.e. its length l and its radius $r_c$, are selected as a function of the dimensions of the diaphragm 22 and the nature of the material of which it is formed, in such a manner as to obtain a cutoff frequency $f_o$ allowing pressure to be measured under normal operating conditions of the sensor but preventing the transmission to the diaphragm of pressure shocks liable to result in bursting.

More specifically, the forces of viscosity present in the restriction 44 can be likened to an electrical resistance R and the compliance of the diaphragm 22 ensuring the storage of a certain volume of oil can be likened to an electrical capacitor C. The assembly constituted by the capillary tube 42 and the deformable diaphragm 22 thus forms a first order mechanical filter comparable to an electrical system of resistance R and capacitance C. This analogy allows the following equations to be written:

$$R=(8 \cdot n \cdot l)/(\pi \cdot r_c^4) \qquad (1)$$

where:

n represents the viscosity of the oil present in the passage 18 at ambient temperature (in Pa.s);

l represents the length of the capillary tube restriction 44 (in mm); and $r_c$ represents the radius of the capillary tube restriction 44 (in mm); and $$C=(r_s^6)/(8 \cdot E \cdot e^3) \qquad (2)$$

where:

$r_s$ represents the radius of the active part of the diaphragm 22 (in mm);

e represents the thickness of the diaphragm 22 (in mm); and

E represents the Young's modulus of the diaphragm 22, in Pa.

In such a system, the cutoff frequency $f_o$ is given by the equation:

$$f_O=1/(2\pi \cdot R \cdot C) \qquad (3)$$

Combining equations (1), (2) and (3) leads to the following equation:

$$r_c^4/l=2 \cdot n \cdot r_s^6 \cdot (f_o/E \cdot e^3) \qquad (4)$$

By fixing the value of the cutoff frequency $f_O$, in the manner previously indicated, at a value lying between the maximum frequency for normal operation of the sensor and the maximum mechanically-acceptable frequency for the diaphragm 22, the values which can be adopted for a given diaphragm 22 of the length l and radius $r_c$ of the restriction 44 can be determined.

More specifically, this restriction 44 is preferably given maximum possible length, given the space available in the smaller diameter section of the tubular part 30, in order to be able to give the radius $r_c$ of the restriction 44 a value suitable for mechanical machining.

As an illustration, a gradiomanometer usually moves in a well at a speed that is low enough for correct operation of the sensor in the course of measurements to be ensured at ambient temperature by a cutoff frequency equal to not more than 100 Hz and preferably equal to about 10 Hz. The choice of such a cutoff frequency makes it possible to avoid a pressure wave resulting from mechanical shock being applied to the diaphragm 22. As a result, practically all risk of bursting the diaphragm under the effect of a shock is avoided. This has been confirmed by tests showing that dropping a gradiomanometer incorporating a pressure sensor like that which has been described with reference to FIG. 2 through a distance of 1 m results in the application to the sensor of a pressure peak only in the region of $25\times10^3$ Pa, which is of no consequence to the integrity of the diaphragm 22.

Equation (4) above shows that the dimensions of the diaphragm 22 are a key parameter for anti-shock protection of this diaphragm. Thus the use of a diaphragm of large size allows it to be protected from shocks with the aid of a restriction 44 whose diameter can be relatively large. Under these conditions, the capillary tube 42 is easy to make.

In contrast, when the dimensions of the diaphragm 22 are too small (for example 1 mm× 1 mm), ordinary machining techniques do not allow a sufficiently narrow restriction 44 to be made to ensure effective protection of the diaphragm. In this case the second embodiment of the invention is advantageously used, and this is now described with reference to FIGS. 3 and 4.

In this second embodiment of the invention the general structure of the differential pressure sensor 20 is identical to that of the sensor described above with reference to FIG. 2, save for the integrated anti-shock protection means. Therefore, only a brief recapitulation of the main parts making up the sensor is given.

Figure 3:
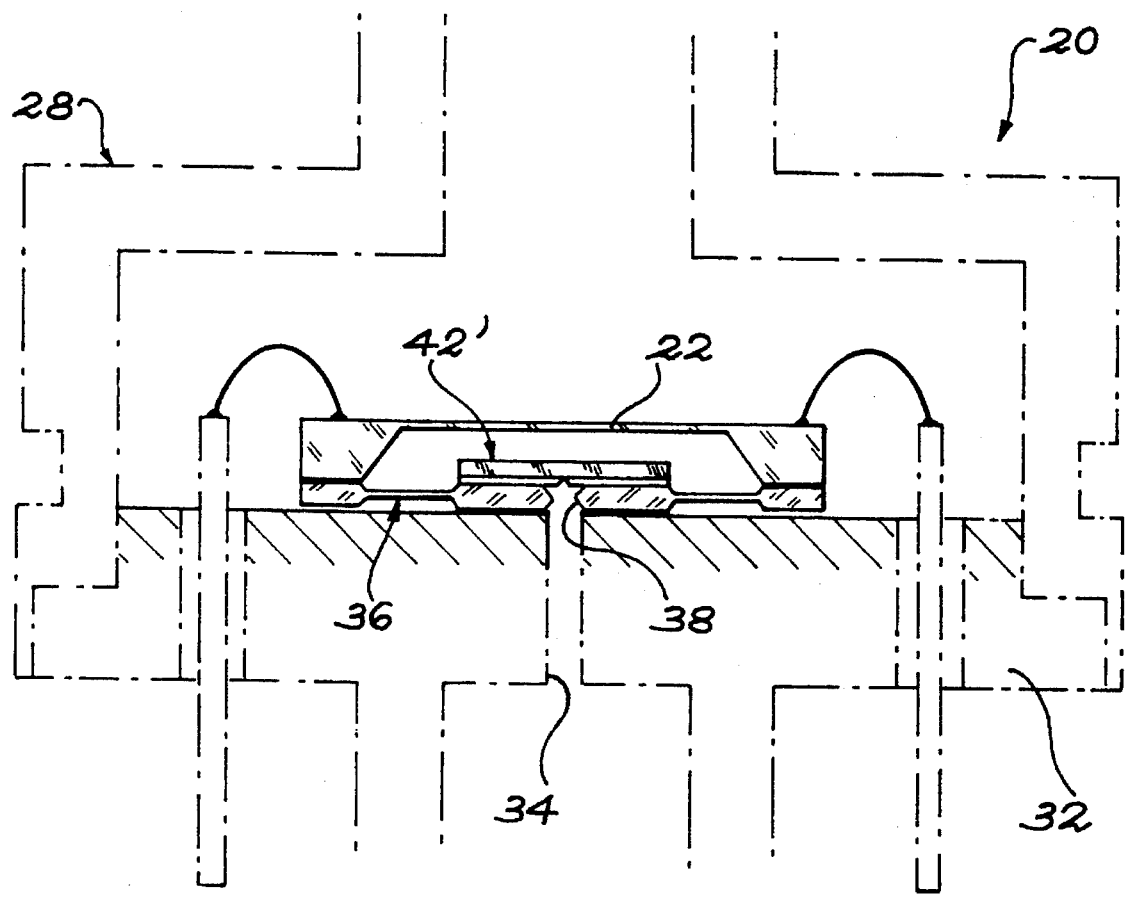
FIG. 3 is a view comparable to FIG. 2 showing a differential pressure sensor constituting a second embodiment of the invention.

As shown in FIG. 3, the differential pressure sensor 20 comprises a tubular support 28 whose structure is the same as that of the support 28 described with reference to FIG. 2. The part 32 in the form of a disk likewise carries the deformable diaphragm 22 via a decoupling part 36. This decoupling part 36 has a central opening 38 located in front of a passage 34 passing through the part 32.

Figure 4:
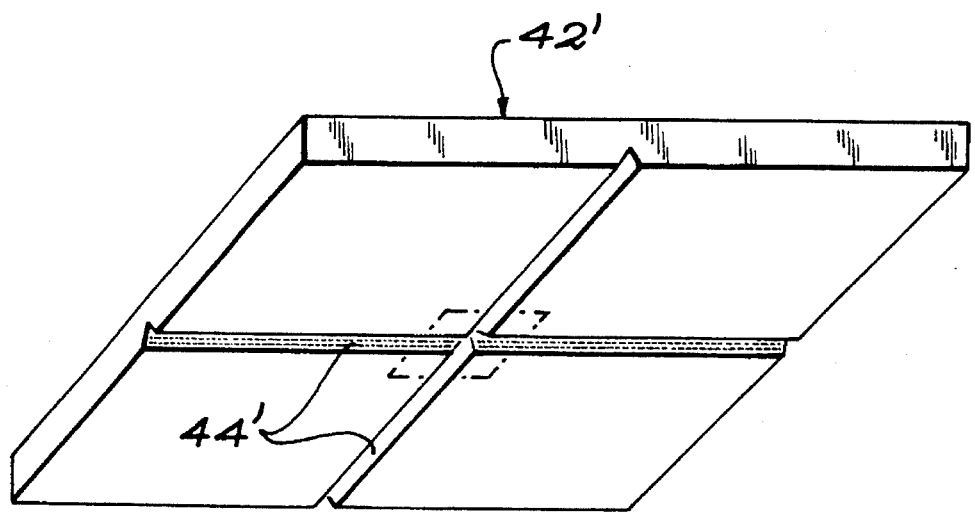
FIG. 4 is an enlarged perspective view showing the grooves formed in the lower face of a small plate incorporated in the sensor of FIG. 3, for forming a restriction.

In this embodiment of FIGS. 3 and 4, the integrated anti-shock protection means is implemented by a small silicon plate 42' bonded onto the upper plane face of the central portion of the decoupling part 36, by means of which this part is itself bonded to the part 32 in the form of a disk.

As shown to a larger scale in FIG. 4, the small plate 42' is without any opening but has grooves 44' in its plane lower face bonded to the plane upper face of the central portion of the decoupling part 36, the grooves forming a restriction through which the central opening 38 in the decoupling part 36 communicates with the space formed between the decoupling part and the diaphragm 22. It is noted that, in a variant, the grooves 44' could be formed in the plane upper face of the central portion of the decoupling part, the plane lower face of the small plate 42' then being without grooves.

The machining of the grooves 44' can be effected by the techniques used in microelectronics, such that the section of the passage of the restriction thus formed can have a very precise value that is subject to practically no lower limit.

In FIG. 4 there is shown the case in which the restriction is obtained by forming two grooves 44' oriented at 90° to each other, intersecting the longitudinal axis of the tubular support 28 and opening at each of the edges of the small plate 42'. More or fewer grooves opening at one of their ends only may equally be used. Moreover, the grooves illustrated in FIG. 4 are of triangular section, but it will readily be understood that a different section (semi-circular, trapezoidal, rectangular, etc.) may be adopted without departing from the ambit of the invention.

The section of the passage through the restriction formed by the groove or grooves 44' is determined in the same manner as the section of the restriction 44 in the embodiment of FIG. 2, by considering a circular hole of radius $r_c$ and length l equivalent to the passage or passages thus formed.

Since it is possible to make the grooves 44' with a section that can be as small as is necessary, the use of a small plate 42' is recommended in all cases in which the dimensions of the diaphragm 22 do not allow use of a capillary tube 42 as illustrated in FIG. 2.

In a modified version (not shown) of the embodiment described with reference to FIGS. 3 and 4, the decoupling part 36 is omitted. The small plate 42' is then fixed directly on the radial face of the part 32, which then carries the deformable diaphragm 22 directly. More specifically, the small plate 42' is fixed on the extension of the passage 34 which passes through the part 32, in such a manner that the passage 34 communicates with the peripheral edges of the small plate 42' through the grooves 44' formed therein or in the adjacent radial face of the part 32.

As the two above-described embodiments show, the restriction can be placed on either side of the diaphragm, in the passage closed by the latter, and at a distance which is not necessarily very near to the diaphragm.

We claim:

1. A pressure sensor comprising a deformable diaphragm closing a fluid passage in sealed manner, and means for measuring deformation of the diaphragm, said passage including a restriction so designed as to co-operate with the diaphragm to form a lowpass filter with a determined cutoff frequency ($f_o$).

2. A sensor according to claim 1, wherein the restriction, implemented as a circular orifice of radius $r_c$ (in mm) and of length l (in mm), satisfies the equation:

$$r_c^4 l = 2 \cdot n \cdot r_s^6 \cdot f_{o_l} E \cdot e^3$$

where:

n is the viscosity of the fluid at ambient temperature (in Pa.s);

r is the useful radius of the diaphragm (in mm);

$f_o^s$ is the cutoff frequency (in Hz) adopted for the sensor;

E is the Young's modulus (in Pa) of the diaphragm; and e is the thickness of the diaphragm (in mm).

3. A pressure sensor according to claim 2, wherein the cutoff frequency $f_o$ lies between a maximum frequency for normal operation of the sensor and a maximum mechanically-acceptable frequency for the diaphragm.

4. A pressure sensor according to claim 3, wherein the cutoff frequency is not more than 100 Hz.

5. A pressure sensor according to claim 4, wherein the cutoff frequency is about 10 Hz at ambient temperature.

6. A pressure sensor according to claim 1, wherein the deformable diaphragm is mounted in a rigid tubular support delimiting a section of said passage internally, the said restriction being formed in this section.

7. A pressure sensor according to claim 6, wherein the restriction is formed by a detachable capillary tube mounted in said section.

8. A pressure sensor according to claim 6, wherein the rigid tubular support has a radial surface on which the deformable diaphragm is fixed via a decoupling part with a central opening communicating with said section, a small plate being fixed on a central portion of the decoupling part and at least one groove defining said restriction being formed in one of the parts constituted by the small plate and the decoupling part, in such a manner as to connect the central opening to a peripheral edge of the small plate.

9. A pressure sensor according to claim 8, wherein the deformable diaphragm, the decoupling part and the small plate are made of silicon.

10. A pressure sensor according to claim 6, wherein the rigid tubular support has a radial surface on which the deformable diaphragm is directly fixed, a small plate being fixed on this radial surface in the continuation of said section of the passage, and at least one groove defining said restriction being formed in one of the parts constituted by the small plate and the rigid tubular support, in such a manner as to connect said section to a peripheral edge of the small plate.

11. A pressure sensor according to claim 10, wherein the deformable diaphragm and the small plate are made of silicon.

12. A pressure sensor according to claim 1, wherein the means for measuring a deformation of the diaphragm comprise a bridge of piezo-resistive strain gages carried by the diaphragm.

13. A pressure sensor according to claim 2, wherein the means for measuring a deformation of the diaphragm comprise a bridge of piezo-resistive strain gages carried by the diaphragm.

14. A pressure sensor according to claim 3, wherein the means for measuring a deformation of the diaphragm comprise a bridge of piezo-resistive strain gages carried by the diaphragm.

15. A pressure sensor according to claim 4, wherein the means for measuring a deformation of the diaphragm comprise a bridge of piezo-resistive strain gages carried by the diaphragm.

16. A pressure sensor according to claim 5, wherein the means for measuring a deformation of the diaphragm comprise a bridge of piezo-resistive strain gages carried by the diaphragm.

17. A pressure sensor according to claim 6, wherein the means for measuring a deformation of the diaphragm comprise a bridge of piezo-resistive strain gages carried by the diaphragm.

18. A pressure sensor according to claim 7, wherein the means for measuring a deformation of the diaphragm comprise a bridge of piezo-resistive strain gages carried by the diaphragm.

19. A gradiomanometer comprising a passage filled with liquid and having ends that open out at two spaced-apart locations, and a differential pressure sensor located in said passage, said sensor comprising a deformable diaphragm closing said passage in sealed manner, and means for measuring deformation of the diaphragm, said passage including a restriction so designed as to co-operate with the diaphragm to form a lowpass filter with a determined cutoff frequency ($f_o$).

20. A gradiomanometer according to claim 19, wherein a bypass duct with a normally-closed valve is connected to said passage, on both sides of the differential pressure sensor, the valve being adapted to open in response to an abrupt displacement of the liquid in the passage.

* * * * *